United States Patent
Weber et al.

(10) Patent No.: US 9,308,078 B2
(45) Date of Patent: Apr. 12, 2016

(54) MEDICAL DEVICE, SYSTEM, AND METHOD FOR REGULATING FLUID FLOW IN BRONCHIAL PASSAGEWAYS

(71) Applicant: Boston Scientific Scimed, Inc., Maple Grove, MN (US)

(72) Inventors: Jan Weber, Maastricht (NL); Aiden Flanagan, Kilcolgan (IE); Torsten Scheuermann, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 76 days.

(21) Appl. No.: 14/255,586

(22) Filed: Apr. 17, 2014

(65) Prior Publication Data
US 2015/0025629 A1 Jan. 22, 2015

Related U.S. Application Data

(60) Provisional application No. 61/856,357, filed on Jul. 19, 2013.

(51) Int. Cl.
*A61F 2/04* (2013.01)

(52) U.S. Cl.
CPC ............. *A61F 2/04* (2013.01); *A61F 2002/043* (2013.01); *A61F 2002/046* (2013.01)

(58) Field of Classification Search
CPC ..... A61F 2/04; A61F 2/203; A61F 2002/046; A61F 2002/043; A61F 2/20; A61M 16/0465; A61M 16/0486; A61M 16/04; A61M 16/0404; A61M 16/0468; A61M 16/0402
USPC ......................................... 623/9, 23.64, 23.65
See application file for complete search history.

(56) References Cited

U.S. PATENT DOCUMENTS

| | | | | |
|---|---|---|---|---|
| 4,100,246 A | * | 7/1978 | Frisch | ...................... A61F 2/04 264/150 |
| 4,787,901 A | * | 11/1988 | Baykut | ................. A61F 2/2412 623/1.26 |
| 8,251,067 B2 | | 8/2012 | Hendricksen et al. | |

FOREIGN PATENT DOCUMENTS

EP 1 359 978 B1 4/2011

* cited by examiner

*Primary Examiner* — Christopher D Prone
*Assistant Examiner* — Rokhaya Diop
(74) *Attorney, Agent, or Firm* — Bookoff McAndrews, PLLC

(57) ABSTRACT

A medical device for regulating fluid flow within one or more lungs of a patient is disclosed. The medical device includes an elongate tubular member, a first extension, a second extension, and a valve member. The elongate tubular member includes a first plurality of channels extending between a proximal and distal ends. The first and second extensions defines a second and third plurality of channels, respectively, each extending from the distal end of the elongate tubular member and configured for placement in a first and second passageway of a lung. The valve member operably couples to the elongate tubular member and is configured to transition between a first position and a second position. The valve member prevents fluid flow to first set of the first plurality of channels in the first position and prevents fluid flow to second set of the first plurality of channels in the second position.

17 Claims, 7 Drawing Sheets

MEDICAL DEVICE, SYSTEM, AND METHOD FOR REGULATING FLUID FLOW IN BRONCHIAL PASSAGEWAYS

CROSS-REFERENCE TO RELATED APPLICATIONS

This application claims the benefit of priority from U.S. Provisional Application No. 61/856,357, filed on Jul. 19, 2013, which is incorporated by reference herein in its entirety.

FIELD

The present disclosure relates generally to devices and methods for use in performing pulmonary procedures and, more particularly, to devices and methods for regulating fluid flow (e.g., air) into and out of bronchial passageways.

BACKGROUND

Chronic obstructive pulmonary disease (COPD) is a respiratory condition that often reduces the ability of one or both lungs to expel air completely during the exhalation phase of the breathing cycle. Such disease is accompanied by chronic or recurrent obstruction to air flow within the lung. COPD may be accompanied with complications such as chronic bronchitis, bronchiectasis, asthma, and/or emphysema. Problems may intensify when patients have overlapping characteristics including two or more such complications, for example, emphysema and chronic bronchitis.

Emphysema is a condition of the lung characterized by the abnormal permanent enlargement of the air sacs located distal to the terminal bronchiole, accompanied by the destruction of their walls, and without obvious fibrosis. It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. As a result, air remains trapped in the diseased portions of the lung.

Conventional treatment methods for emphysema include Lung Volume Reduction Surgery (LVRS), which includes surgical removal of the diseased portion of the lung. Recent advances also include devices that isolate a diseased region of the lung in order to reduce the volume of the diseased region, such as by collapsing the diseased lung region. However, such devices are still in the development stages. Thus, there is much need for devices and methods for regulating the flow of air into and out of diseased portions of a patient's lungs.

SUMMARY

Embodiments of the present disclosure are directed to medical devices suitable for use in medical or surgical procedures for treating conditions causing airway distress, such as reversible obstructive pulmonary disease and/or asthma.

In one embodiment, a medical device for regulating fluid flow within one or more lungs of a patient may include an elongate tubular member having a proximal end, a distal end, and a first plurality of channels extending therebetween; a first extension extending from the distal end of the elongate tubular member and configured for placement in a first passageway of a lung, wherein the first extension defines a second plurality of channels in communication with a first set of the first plurality of channels; a second extension extending from the distal end of the elongate tubular member and configured to be disposed in a second passageway of a lung, wherein the second passageway is different from the first passageway, and wherein the second extension defines a third plurality of channels in communication with a second set of the first plurality of channels; and a valve member operably coupled to a proximal end portion of the elongate tubular member, wherein the valve member is configured to transition between a first position and a second position, wherein, in the first position, the valve member is configured to prevent fluid flow in the first set of the first plurality of channels, and, in the second position, the valve member is configured to prevent fluid flow in the second set of the first plurality of channels.

Various embodiments of the medical device may include one or more of the following features: the first and second extensions includes a first leg and a second leg configured to extend away from one another in a distal direction; a portion of the medical device includes a plurality of anchoring members; the anchoring members are disposed on at least one of the first and second extensions; the anchoring members include barbs configured to pierce a tissue of the lung; the medical device is configured to transition between a compressed configuration and an expanded configuration; a portion of the medical device includes a wire scaffolding; at least one of the channels in the first set of the first plurality of channels includes a one-way valve configured to allow fluid to flow in a first direction but not in a second direction opposite to the first direction; the first direction is from the at least one of the first set of the first plurality of channels towards the elongate tubular member; the valve member includes a plurality of arms disposed at an angle relative to one another; the angle between two adjacent arms is one of approximately 90 degrees, an acute angle, or an obtuse angle; the first passageway is configured to be placed in a first lobe of a lung and a second passageway is configured to be placed in a second lobe of a lung; the first and second lobes are part of the same lung; and the first lobe is disposed in a first lung and the second lobe is disposed in a second lung different than the first lung.

In another embodiment, a method for regulating fluid flow within a patient's lung may include delivering a medical device to a bronchial passageway within the patient's lung. The medical device may include an elongate tubular member having a proximal end, a distal end, and a first plurality of channels extending therebetween; a first extension extending from the distal end of the elongate tubular member and configured for placement in a first passageway of the lung, wherein the first extension defines a second plurality of channels in communication with a first set of the first plurality of channels; a second extension extending from the distal end of the elongate tubular member and configured to be disposed in a second passageway the lung, wherein the second passageway is different from the first passageway, and wherein the second extension defines a third plurality of channels in communication with a second set of the first plurality of channels; and a valve member operably coupled to a proximal end portion of the elongate tubular member, wherein the valve member is configured to transition between a first position and a second position, wherein, in the first position, the valve member is configured to prevent fluid flow in the first set of the first plurality of channels, and, in the second position, the valve member is configured to prevent fluid flow in the second set of the first plurality of channels. The method may further include positioning the elongate tubular member in a primary bronchial passageway; positioning the first extension in a first secondary bronchial passageway; and positioning the second extension in a second secondary bronchial passageway.

Various embodiments of the method may include one or more of the following features: the first secondary bronchial passageway is a superior bronchial passageway leading to a first lobe of the patient's lung; the second secondary bronchial passageway is an inferior bronchial passageway leading to a second lobe of the patient's lung, the second lobe being different than the first lobe; and the medical device is configured to transition between a compressed configuration and an expanded configuration.

In another embodiment, a medical device for regulating fluid flow within one or more lungs of a patient may include an elongate tubular member having a proximal end, a distal end, and a first plurality of channels extending therebetween, wherein the elongate tubular member includes a wire scaffolding configured to transition between an expanded configuration and a collapsed configuration, and wherein the elongate tubular member defines a longitudinal axis; at least one extension extending from the distal end of the elongate tubular member and configured for placement in a first passageway of the lung, wherein the at least one extension is disposed at an angle relative to the longitudinal axis of the elongate tubular member, and wherein the at least one extension defines a second set of plurality of channels in communication with a first set of the first plurality of channels; and a valve member operably coupled to a portion of the elongate tubular member, wherein the valve member is configured to transition between a first position and a second position by fluid flowing through the elongate tubular member, wherein, in the first position, the valve member is configured to prevent fluid flow in the first set of the first plurality of channels.

Various embodiments of the medical device also may include a second extension extending from the distal end of the elongate member and configured for placement in a second passageway of the lung, wherein the second passageway is different than the first passageway.

It may be understood that both the foregoing general description and the following detailed description are exemplary and explanatory only and are not restrictive of the invention, as claimed.

DETAILED DESCRIPTION OF THE DRAWINGS

The accompanying drawings, which are incorporated in and constitute a part of this specification, illustrate exemplary embodiments of the present disclosure and together with the description, serve to explain principles of the disclosure.

Figure 2:
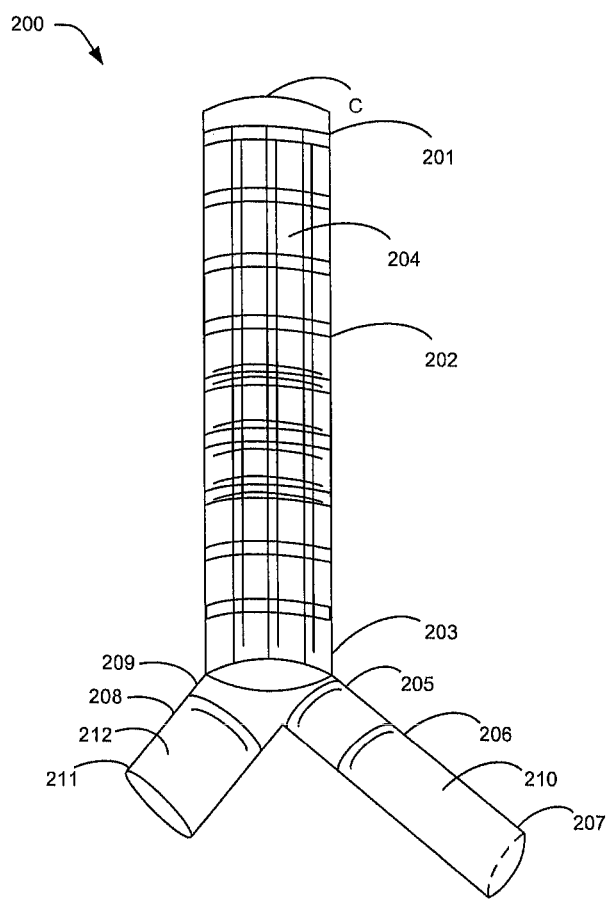
FIG. 2 is a schematic view of the medical device of FIG. 1A.
Figures 4A, 4B, 4C:
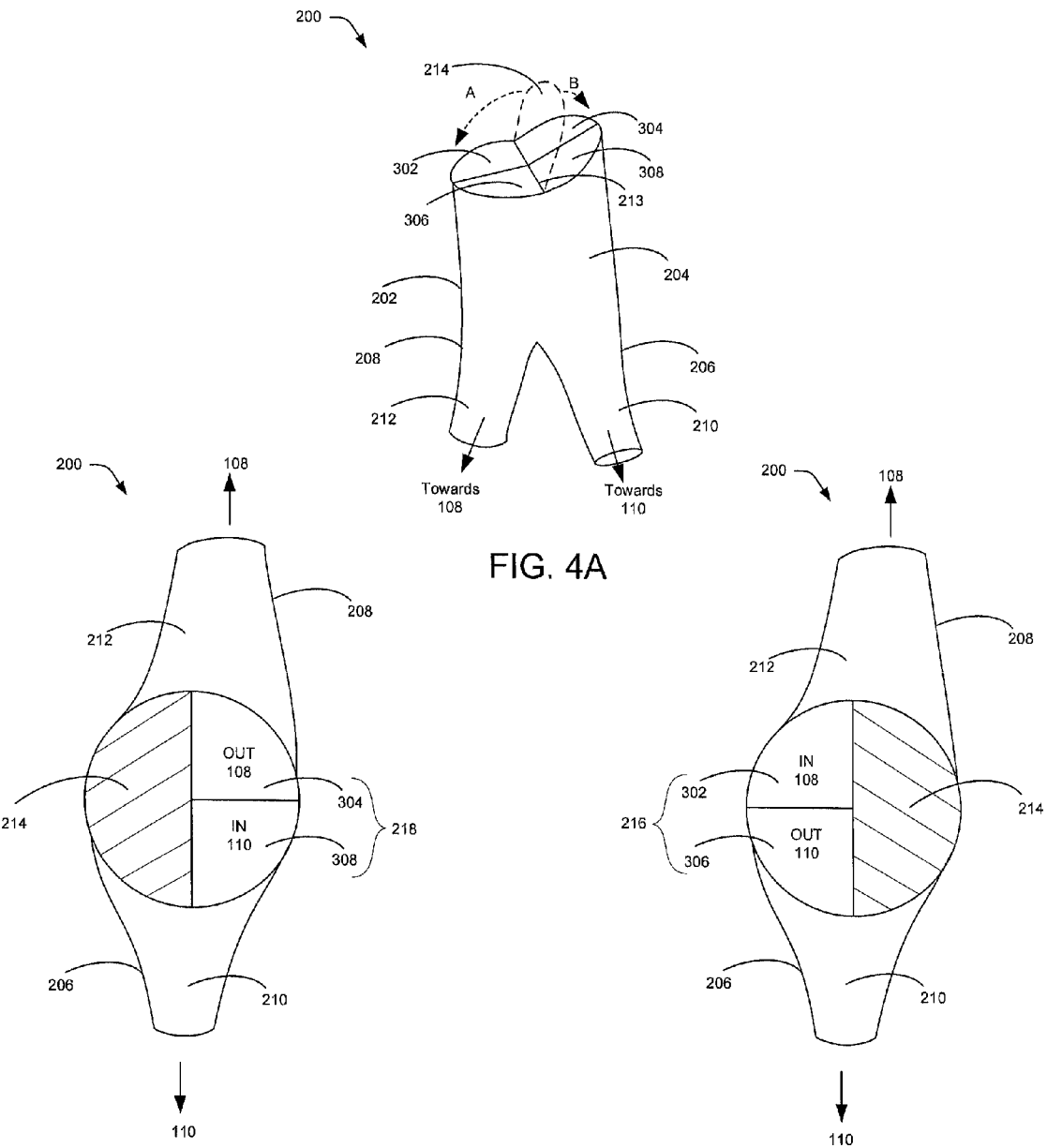

FIGS. 4A, 4B, and 4C are schematic views illustrating an exemplary operation of the medical device shown in FIG. 2.

Figure 5:
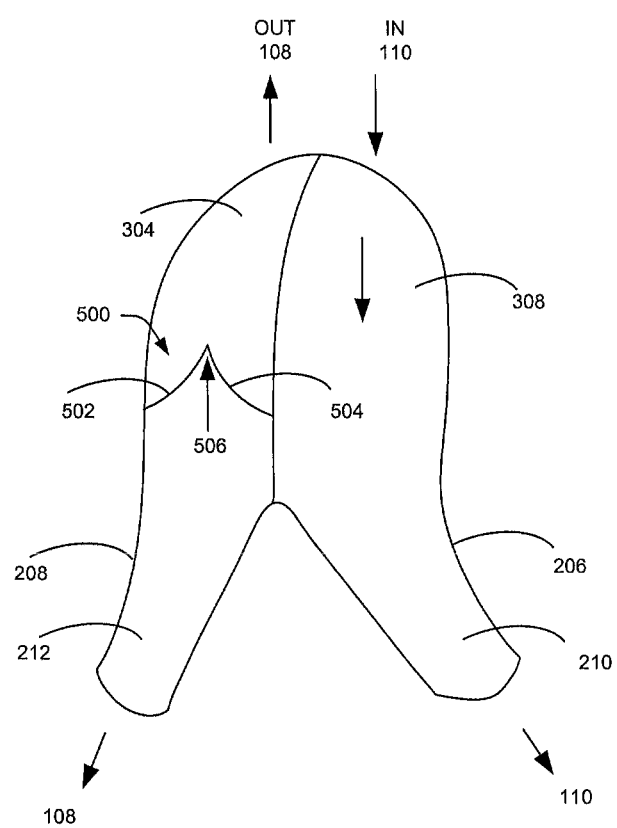

FIG. 5 shows an embodiment of the medical device having a one-way valve.

Figures 6, 7:
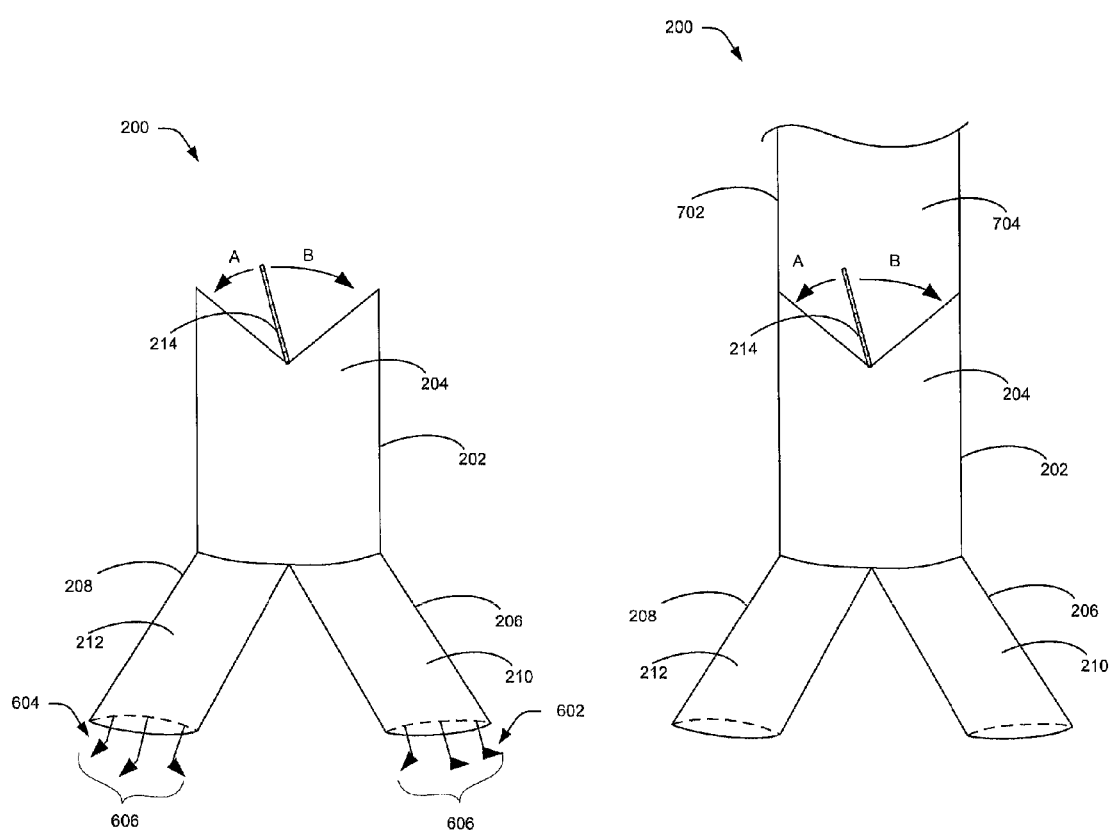

FIG. 6 shows another embodiment of the medical device having a securing mechanism.

FIG. 7 shows yet another embodiment of the medical device having a sheath attached thereto.

Figure 8A:
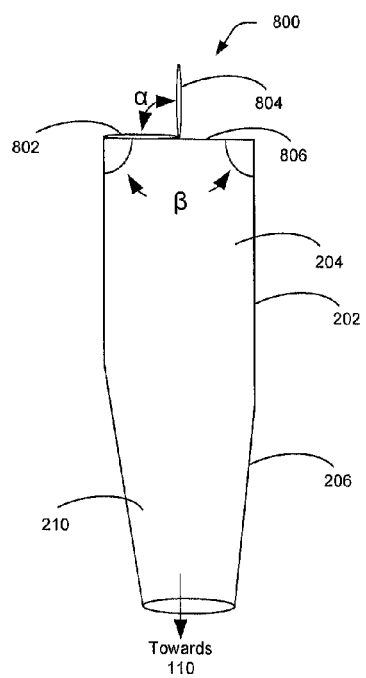
Figure 8B:
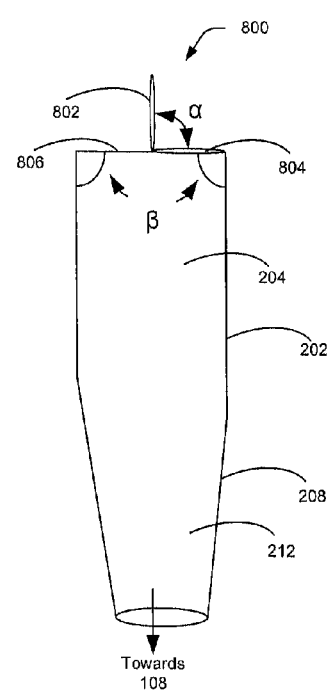
Figure 8C:
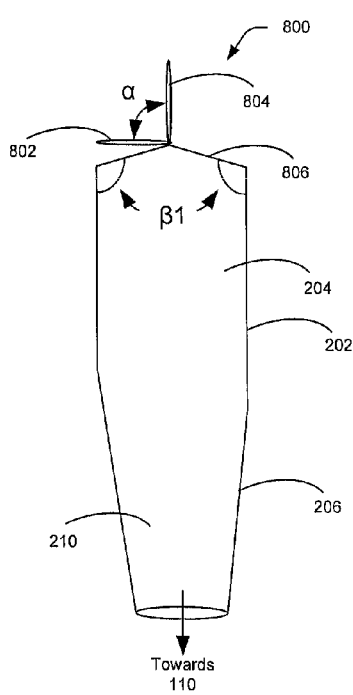

FIGS. 8A, 8B, and 8C illustrate another embodiment of the medical device having a rocker valve member.

DESCRIPTION OF EXEMPLARY EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device into a patient. By contrast, "proximal" refers to the end closest to the medical professional when placing a device in the patient.

Overview

The present disclosure is directed to medical devices and methods for performing pulmonary procedures. More particularly, the disclosure relates to devices and methods for treating various lung diseases, such as, emphysema and Chronic Obstructive Pulmonary Disease (COPD), and otherwise improving lung function. One embodiment includes a medical device configured to regulate fluid (e.g., air) flow into and out of one or more lung regions. To accomplish this, the medical device can employ a valve that allows intermittent or alternative inflation and deflation of a first lung region and a second lung region. One effect of temporarily closing off certain lobes of a lung is that adjacent lobes are allowed to inflate more effectively, similar to more invasive surgical procedures in which portions of the lung may be removed.

According to an example, when positioned in a hollow structure in a patient's body, such as a bronchiole in one of the lungs, the medical device may be configured to allow fluid flow into a first lung region and control (e.g., meter and/or prevent) fluid flow into a second lung region. To accomplish this, the valve closes the second lung region to maintain the second lung region in a decompressed or non-operative state. This prevents expansion or hyper-expansion of any diseased tissue of or associated with the second lung region. In addition, closing of the second lung region may allow lung tissue associated with the first region to inflate effectively. In an alternating fashion, similarly, once the fluid exits the first lung region upon exhalation, the medical device may adjust configuration to allow fluid to flow into the second lung region to inflate the tissue of second lung region effectively while closing off fluid flow to the first lung region.

As used herein, controlled fluid flow includes, but is not limited to, the flow of fluid being altered in some manner such as to restrict or otherwise preclude the flow in the second region. To this end, the medical device may regulate the fluid flow to, for example, completely block, substantially block, partially block, limit, meter, or regulate fluid flow into the one or more lung regions using embodiments of the devices disclosed herein.

Further, throughout this disclosure, reference is made to the term "lung region". The term "lung region" refers to a defined portion or section of a lung. For purposes of example, lung regions are described herein with reference to human lungs, wherein some exemplary lung regions include lung lobes and/or lung segments. Thus, the term "lung region" as used herein can refer, for example, to a lung lobe or a lung segment. Such nomenclature conforms to nomenclature for portions of the lungs that are known to those skilled in the art. However, it should be appreciated that the term "lung region" does not necessarily refer to a lung lobe or a lung segment, but can refer to some other defined naturally occurring or otherwise created division or portion of a human or non-human lung. A "lung region" may also refer to an entire lung, such as, e.g., a left lung of a patient.

Exemplary Embodiment

Figures 1A, 1B:
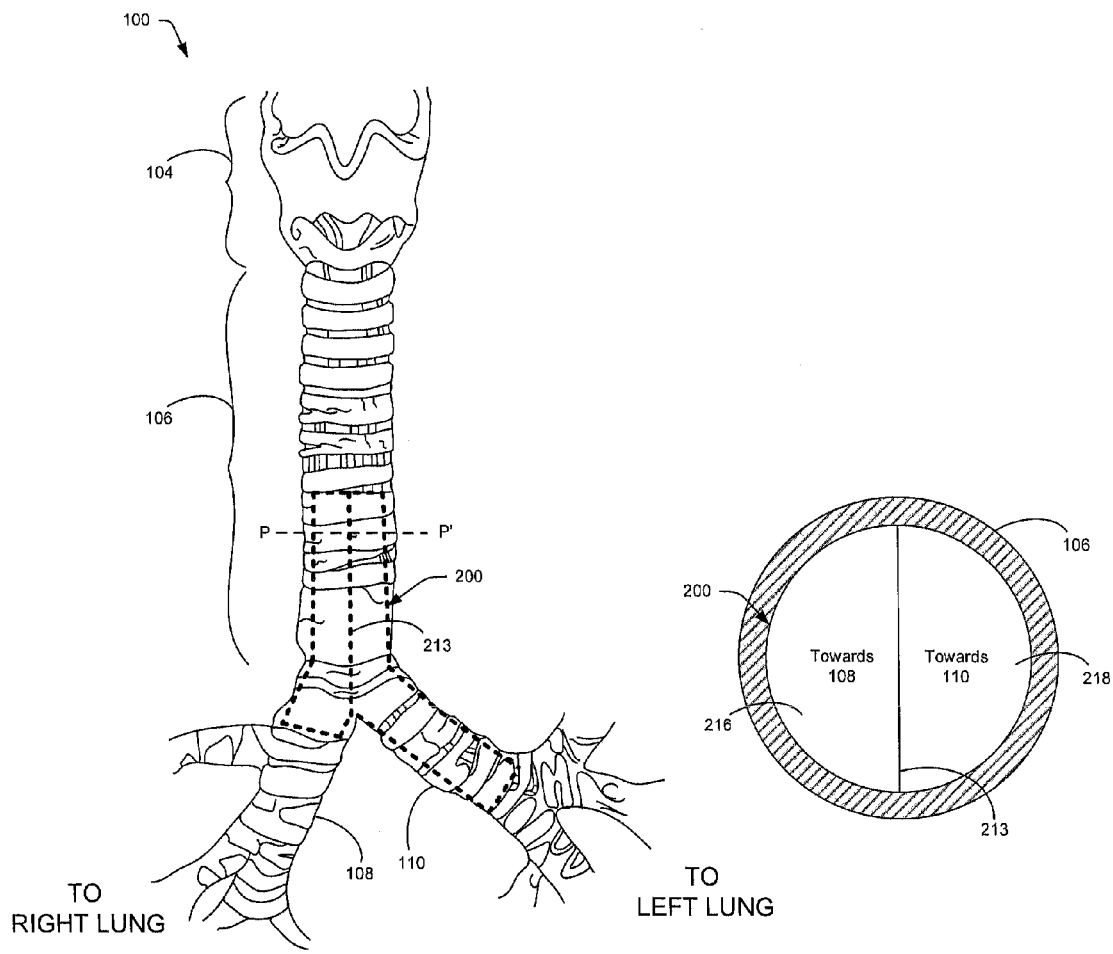
FIG. 1A is a schematic view of an exemplary medical device disposed in a bronchial passageway, according to an embodiment of the present disclosure.
FIG. 1B is a sectional view of the medical device of FIG. 1A taken along a plane P-P' in FIG. 1A.

FIG. 1A is a schematic view of an exemplary medical device 200 disposed within a bronchial passageway 100 of a patient. In particular, the medical device 200 is located within a trachea 106 of the patient such that at least a portion of the medical device 200 also extends to a portion of a right primary bronchus 108 and a left primary bronchus 110. It may be contemplated that the medical device may be advanced through the larynx 104 to be placed within the trachea 106. The medical device 200 may be maneuvered or navigated to the trachea 106 using any suitable device(s) that are conventionally known. Examples of such device(s) may include a bronchoscope, a delivery sheath, or the like.

The medical device 200 may be configured to regulate flow of a fluid (e.g., air) in one or more directions through medical device 200. With reference to embodiments of the present disclosure, "fluid" means gas, liquid, or a combination of a gas(es) and liquid(s). According to an example, the medical device 200 being placed in the trachea 106 may allow fluid to flow through the trachea 106 and into the right as well as left primary bronchus 108 and 110. In such instances, the medical device 200 may feed a left lung region and a right lung region, where the left lung region is connected to the left primary bronchus and the right lung region is connected to the right primary bronchus. It should be understood that the medical device 200 may be positioned at any suitable location within the bronchial passageway 100 so as to allow fluid to flow into one or more lung regions. To this end, the medical device 200 may be positioned within the bronchi so as to feed two different lobes or segments of a single lung. That is, embodiments of the disclosed medical device 200 may be suitably positioned in a branched airway so as to allow a fluid (e.g., air) to flow into first and second lobes of either the left lung or right lung. Alternatively, the medical device may be positioned within bronchi in order to feed two different segments of a same lobe of either or both of the left lung or the right lung. Although the present disclosure describes medical device 200 as being configured to allow fluid to flow into two portions or segments of a single lung, those of ordinary skill in the art will understand that the fluid may flow into a lesser (e.g., only a single segment or portion) or greater (e.g., three or more segments or portions) segments or portions of one or more lungs, as desired or appropriate.

Further, the medical device 200, shown in more detail in FIG. 2, may have a Y-shaped configuration having a vertical division 213 therein. Although discussed in more detail in subsequent figures, the vertical division 213 bifurcates the medical device 200 along its axis to allow the fluid to flow into the right and left primary bronchus 108 and 110, thereby feeding the left and right lung of the patient. In another embodiment, the vertical division may bifurcate the medical device 200 so that fluid may be delivered into two differing portions of segments of the same lung. In particular, the vertical division 213 may divide the medical device into a first cavity 216 and a second cavity 218 directing the fluid to flow into, e.g., the left and right lung regions, respectively. Those skilled in the art will appreciate that the medical device 200 may have any suitable shape or structure configured to permit fluid to flow in one or more directions. Exemplary shapes may include, yet not are limited to, T-shape, Y-shape, or the like.

Further, medical device 200 may have a plurality of vertical divisions 213 for dividing device 200 along its axis.

Further, a cross-sectional view of the medical device 200 of FIG. 1A along a plane P-P' is shown in FIG. 1B. The medical device 200 may have a substantially circular cross-section. It should be understood, however, that the medical device 200 may have any suitable cross-section such as, for example, rectangular, square, irregular, polygonal, oblong, or the like. In addition, the medical device 200 may be specifically configured to conform to the shape of the body lumen and/or cavity where the medical device 200 is disposed. For instance, as shown in FIG. 1B, the medical device 200 disposed within the trachea 106 substantially conforms to the circular shape of the trachea 106. To facilitate such conforming, medical device 200 may be made of portions having sufficient flexibility to accommodate curves and contours typical of a patient's anatomy, as discussed in greater detail below.

To accomplish this, the material of the medical device 200 may be adapted to have a stiffness to be modified to form the medical device 200 for use in various locations within the bronchial passageway. For instance, the material should exhibit sufficient flexibility to maneuver through the body lumens and be positioned within the bronchial passageway 100 without causing any injury to the surrounding tissue.

According to an example, materials employed to manufacture the medical device 200 may include any suitable biocompatible material such as, but not limited to, polymers, metals, alloys, composites, or the like. Exemplary materials may include silicone, self-expanding alloys such as Nitinol, and so forth. According to an example, a combination of suitable materials may also be combined to form a hybrid medical device 200. For example, medical device 200 may be configured as a stent having cross-linked metal scaffolding made from a shape memory metal alloy such as Nitinol that can be completely, partially, or substantially coated with a polymeric membrane such as polyurethane and/or silicone. In this example, medical device 200 may be a self-expanding stent. Further, the polymeric coating may impart an improved flexibility to the medical device 200, while the metal alloy may provide sufficient strength to the overall structure of the medical device 200 while also allowing for self-expansion due to shape memory characteristics. In certain instances, the medical device 200 may also include any suitable coating. Such coatings may include, but are not limited to, lubricious and/or therapeutic coatings, including, e.g., an anti-microbial coating that may avoid occurrence of immune response in vivo. It is contemplated that any suitable coating may be disposed on any surface of medical device 200. Further, some embodiments of device 200 may be fabricated from materials configured to transition from a first configuration to a second configuration upon exposure to a predetermined trigger, such as, e.g., body temperature and/or chemistry. Such materials may include one- or two-component glues, hardening agents, and/or ultraviolet or heat reactive substances. For example, it is contemplated that medical device 200 may be inserted into a patient's airway in a first configuration (e.g., a relatively compliant or configuration) and then transitioned to a second configuration (e.g., a relatively hardened configuration) upon exposure to a trigger and after an outer surface of medical device 200 has conformed to the airway.

Turning now to FIG. 2, a schematic view of the medical device 200 of FIG. 1A is shown. The medical device 200 may include an elongate tubular member 202 having a proximal portion 201 having an opening, a distal portion 203 having an opening, and a through lumen 204 extending between the openings in the proximal 201 and distal 203 portions. The medical device 200 can further include a first leg 206 and a second leg 208 coupled to and extending distally from the distal portion 203 of the elongate tubular member 202, thereby forming the Y-shaped or any other suitable configuration. More particularly, legs 206 and 208 may extend at predetermined angles relative to one another and to tubular member 202. For example, legs 206, 208 may define an angle of approximately 90 degrees between each other. Legs 206, 208 may be substantially similar to one another or may include differing configurations. For example, in some embodiments, one of legs 206, 208 may include a larger length or diameter than the other of legs 206, 208. Details of each component of the medical device 200 will now be discussed.

The elongate tubular member 202 may be a generally elongate and hollow member having a circular cross-section. Alternatively, cross-sectional shapes including cylindrical, rectangular, oval, or other suitable shapes also may be contemplated as appropriate for use in the intended environment. Although the elongate tubular member 202 defines a single lumen 204, the tubular member 202 may define a plurality of lumens (not shown), with some of the plurality of lumens extending the entire length of the tubular member 202, and the remaining lumens only extending partly through tubular member 202.

As alluded to above, the elongate tubular member 202 can further include a hermetic partition such as, e.g., vertical division 213, (as shown in FIG. 1B) that divides the lumen 204 into at least two cavities 216 and 218 (as shown in FIG. 1B). The two cavities 216 and 218 may be configured to be in fluid communication with legs 206 and 208, respectively, thereby permitting the fluid to flow through the first leg 206 and the second leg 208, respectively. Further details of the two cavities 216 and 218 will be discussed with respect to FIG. 3B below.

The dimensions of the elongate tubular member 202 may be adapted to conform to the inner trachea 106 wall. For instance, an outer diameter of the elongate tubular member 202 may be substantially the same as or slightly smaller than the inner diameter of the trachea 106. Those skilled in the art will understand that the inner wall of the trachea 106 includes cartilaginous rings that may lead to an irregular inner wall texture of the trachea 106. To this end, the elongate tubular member 202 may be made from a flexible material so as to conform to the inner wall of the trachea 106 or any other passageway of a lung, including, but not limited to, bronchia. Similarly, legs 206 and 208 also may be configured to conform to portions of the trachea 106 or one or more generations of bronchia. Alternatively, the elongate tubular member 202 may include an outer coating or geometric structure(s) configured to conform to the irregular inner wall of trachea 106. Exemplary structures may include grooves, ridges, projections, or the like. Further, elongate tubular member 202 and/ or each of first and second legs 206, 208 may include any suitable cross-section configuration and corresponding external geometries. For example, as those of ordinary skill in the art recognize, e.g., the trachea and the first and second generation bronchia may include a D-shaped passageway. Accordingly, one or more of elongate tubular member 202, first leg 206, and second 208 may include a corresponding configuration, such as a corresponding D-shaped configuration.

Further, the proximal portion 201 of the elongate member 202 may include at least one curved section C that may improve sealing of the elongate tubular member 202 with the bronchial passageway 100, in particular, the trachea 106. In an embodiment, one or more curved sections C may be disposed in an alternating fashion along the periphery of the proximal portion 201. Two such curved sections 215 and 217 will be discussed in detail with respect to FIG. 3A. Furthermore, although not shown, the medical device 200 may also include one or more grooves made on an external surface of the elongate tubular member 202, which may further improve the sealing of the elongate tubular member 202 against the cartilaginous rings of the trachea 106.

As alluded to above, the first leg 206 may have a proximal end 205 operably coupled to the distal portion 203. The first leg 206 may further define a lumen 210 extending between the proximal end 205 and a distal end 207. The lumen 210 may remain in fluid communication with the lumen 204. Further, as shown in FIG. 1A, the first leg 206 may be disposed within the left primary bronchus 110 adapted to permit flow of the fluid to a left lung region. It should be contemplated that the left lung region may include the upper and lower lobes of the left lung. In addition, lumen 210 may be replaced with two or more lumens.

Similarly, the second leg 208 may have a proximal end 209, a distal end 211, and a lumen 212 disposed therebetween. Lumen 212 may include two or more lumens as desired. The second leg 208 also may be coupled to the distal portion 203 such that the lumen 212 may remain in fluid communication with the lumen 204. The second leg 208 may be disposed within the right primary bronchus 108 adapted to permit fluid to flow to a right lung region. Here, the right lung region may include upper, middle, and lower lobes of the right lung.

Further, the direction of fluid flow, which may be either to the first leg 206 or to the second leg 208, may be controlled by a valve member 214, which will now be discussed in detail with respect to FIGS. 3A and 3B. The embodiments of the present disclosure may be referenced or described by the use of terms like "inhalation direction" and "exhalation direction". As used herein, the "inhalation direction" may be defined as, e.g., a direction of fluid flowing towards the lungs with respect to the nostrils, which may occur when a person inhales during a respiratory cycle. In contrast, the "exhalation direction" may be defined as, e.g., a direction of fluid flowing away from the lungs towards the nostrils, which may occur when a person exhales during a respiratory cycle.

Figure 3A:
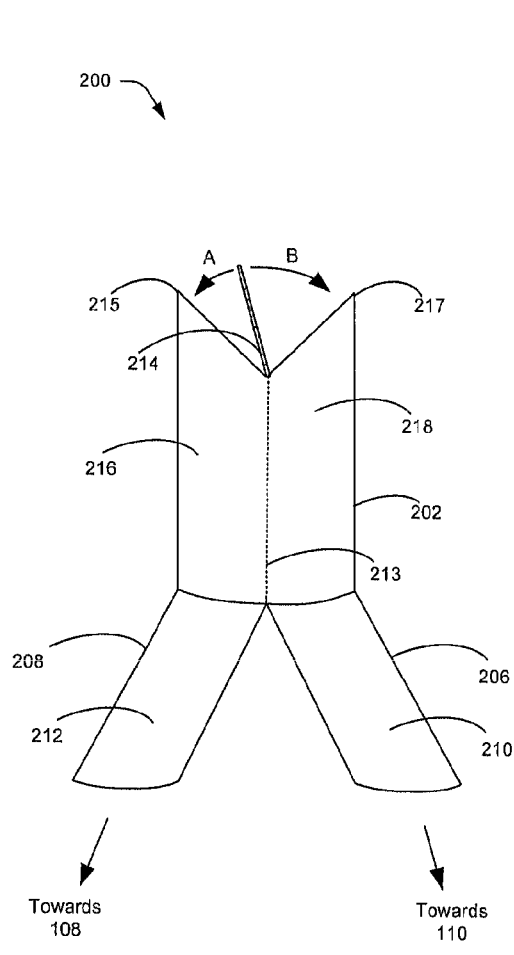
FIG. 3A is a lateral view of an embodiment of a medical device, according to an aspect of the present disclosure.

Referring to FIG. 3A, a schematic view of the medical device 200 including the valve member 214 is depicted. The valve member 214 may include a suitably configured member coupled to a proximal end of the elongate tubular member 202. Valve member 214 also may be coupled to any other suitable portion of tubular member 202. In one embodiment, the valve member 214 may be configured to pivot about a hinge (or other suitable coupling) on a proximal end of tubular member 202. The valve member 214 may include a flip-flop design, which may be configured to allow valve member 214 to transition between a first position and a second position. According to an example, the valve member 214 may be adapted to transition towards a first direction A to contact the curved section 215 in the first position. In addition, the valve member 214 may be configured to transition towards a second direction B to contact the curved section 217 in the second position. Sections 215 and 217 may include any suitable configuration known in the art, including, e.g., substantially planar configurations.

To this end, the valve member 214 in the first position (e.g., fully disposed in direction A against a proximalmost surface of section 215) may restrict inhaled fluid from entering into cavity 108 and, consequently, into the lumen 212 of second leg 208. As a result, this configuration permits the inhaled fluid to enter into first cavity 110 of the lumen 210 of first leg 206. Alternatively and additionally, the valve member 214 in the second position (e.g., fully disposed in direction B) may restrict the fluid from entering into the lumen 210 of first leg 206. As a result, this configuration permits the fluid to enter in the lumen 212 of second leg 208. Further details of the valve member 214 along with the first A and second B positions of the valve member 214 will be discussed now with respect to the FIG. 3B.

Figure 3B:
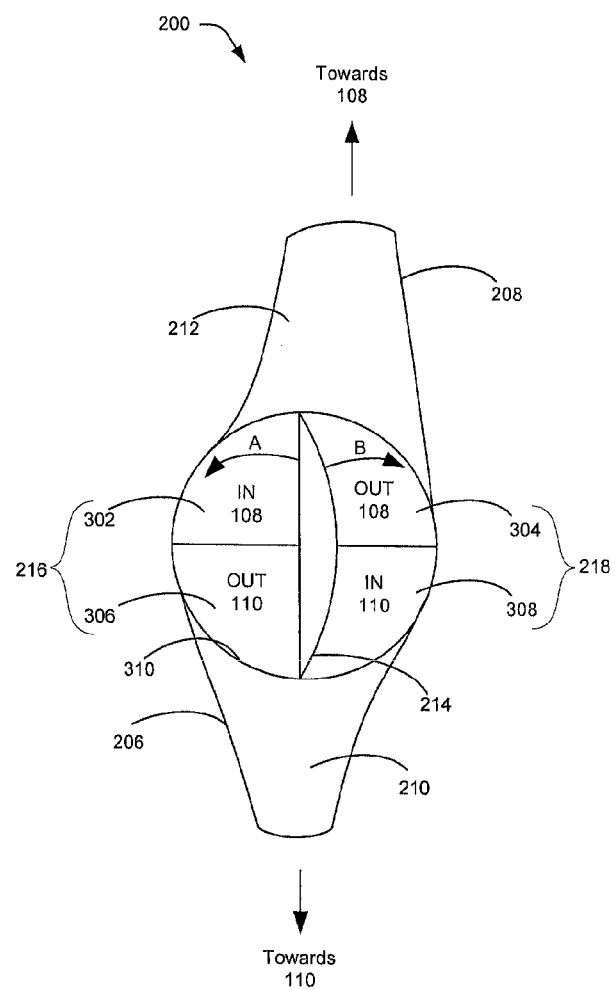
FIG. 3B is a top view of the medical device of FIG. 3A.

Referring now to FIG. 3B, the valve member 214 may include a substantially semi-circular shape, which can be operably coupled to a top (e.g., proximalmost) surface 310 of the elongate tubular member 202. Valve member 214 also may include any suitable configuration known in the art. The valve member 214 may be coupled to the top surface 310 using any suitable means, method, or structure known in the art. Exemplary means, methods, and structures may include welding, soldering, gluing, threading, attachment via attachment structure, attachment via an integral "living hinge" formed during molding or other manufacturing process such that the valve member 214 includes an integral one piece and continuous configuration with the top surface 310 and/or remainder of the medical device 200. Valve member 214 may include any suitable configuration known in the art for directing the flow of fluids such as, e.g., air. Furthermore, in some embodiments, valve member 214 may be removably or temporarily secured to a respective surface of sections 215 and/or 217. For example, in one embodiment may be attracted held against a surface of, e.g., section 217 by a mechanical coupling, a magnetic attraction, or any other suitable means known in the art. In addition, valve member 214 may be configured to be biased (e.g., slightly biased) towards one or both of section 215, 217 by, e.g., a suitable resilient member including, but not limited to, a leaf spring. The leaf spring may be configured to couple valve member 214 to elongate tubular member 202. In this manner, operation of valve member 214 may be improved with the assistance of gravity and/or the resilient forces exerted by a resilient member. Thus, once valve member 214 is disposed closer to one of sections 215, 217 than the other of sections 215, 217, the forces exerted on valve member 214 may serve to urge valve member 214 towards the section it is closer to.

In one embodiment, the valve member 214 may be coupled to the top surface 310 so as to remain parallel along the vertical axis of the elongate tubular member 202. More specifically, the valve member 214 may remain parallel to the vertical division 213 (as shown in FIG. 1B), while being in contact with the vertical division 213. It should be noted that the semi-circular shape of the valve member 214 may be opted to cover the first or the second cavity 216 and 218 formed by the vertical division 213. More specifically, the valve member 214 may substantially cover the first cavity 216 in the first position, while covering the second cavity 218 in the second position. To this end, a radius of the semi-circular valve member 214 should be equal to the radius of the two semi-circular cavities 216 and 218. Those skilled in art should, therefore, understand that any suitable shape of the valve member 214 may be adapted to cover the cavities formed by the elongate tubular member 202.

Further, the first cavity 216 may include a first inlet cavity 302 and a first outlet cavity 306, while the second cavity 218 may include a second inlet cavity 308 and a second outlet cavity 304. According to an embodiment, the first inlet cavity 302 permits flow of the fluid to the right primary bronchus 108, whereas the second inlet cavity 308 permits flow of the fluid to the left primary bronchus 110. It should be noted that the fluid entering the first inlet cavity 302 during inhalation comes out through the second outlet cavity 304 upon exhalation, whereas the fluid entering the second inlet cavity 308 upon inhalation comes out through the first outlet cavity 306 during exhalation. Therefore, this inhale-exhale cycle allows continuous switching of the valve member 214 between the first state and the second state.

In addition, at least one of the inlet cavities 302 and 308 remains substantially (e.g., totally or almost totally) closed during the respiratory cycle. For example, closing of the first inlet cavity 302, when the valve member 214 is in the first position A, allows the fluid to enter the second inlet cavity 308. Further, the fluid passes through the lumen 210 of the first leg 206 to feed a first region of a lung, thereby allowing the first region to inflate effectively, while avoiding hyperinflation and/or air-trapping within a second region of a lung. Similarly, closing the second inlet cavity 308, when the valve member 214 is in the second position B, allows the fluid to enter the first inlet cavity 302. Further, the fluid passes through the lumen 212 of the second leg 208 to feed a second region of the lung, thereby allowing the second lung region to inflate effectively, while avoiding hyperinflation and/or air-trapping within the first lung region. The first and second lung regions may be portions of the same lung or may be portions of differing lungs. For example, in embodiments where the first and second lung regions are portions of the same lung, the first region may be a first lobe and the second region may be a second lobe, wherein the first and second lobes may be disposed adjacent to one another.

Turning now to FIGS. 4A-4C, an implementation of the working of valve member 214 to transition between the first and second states (e.g., positions A and B) is shown. As shown in FIG. 4A, the valve member 214 is capable of switching between the first position (e.g., disposed completely in the direction A) and the second position (e.g., disposed completely in the direction B). In some embodiments, the valve member 214 may be configured to transition between said two states based on a variety of factors. Exemplary factors may include 1) volume of the fluid (e.g., air) inhaled 2) direction of flow of the fluid, or the like.

Further, FIG. 4B shows a schematic view of the valve member 214 disposed in the first position A. As alluded to above, the valve member 214 in the first position A closes or substantially closes the first cavity 216 including the first inlet cavity 302 and the first outlet cavity 306. In such instances, upon inhalation, the fluid enters through the second inlet cavity 308, and is delivered to a first lung region through the lumen 210 of first leg 206.

During exhalation, inhaled fluid (e.g., air) may be returned from the first lung region through the lumen 210 of leg 206 towards valve member 214. Due to the presence of another valve (e.g., a one-way valve) disposed in inlet cavity 308 (discussed in greater detail below), the air is exhaled through outlet cavity 306. The exhaled air may act against valve member 214 in the first position A to cause the valve member 214 to transition to the second position B, as shown in FIG. 4C, thereby allowing the fluid to be expelled outside the lung region. In such an instance, the fluid passes through the first outlet cavity 306.

Once valve member 214 is in the second position B, fluid (e.g., air) inhaled during a subsequent respiratory cycle may enter through the first inlet cavity 302 and pass through the lumen 212 of the second leg 208 so as to be directed to a second lung region. Subsequently, during exhalation and as a result of a one-way valve (discussed below in greater detail) disposes in inlet cavity 302, the fluid may be exhaled through the second outlet cavity 304, thereby once again switching the valve member 214 to the first position A (as shown in FIG. 4B).

The medical device 200 may further include an apparatus or structure, which substantially (e.g., effectively) prevents the fluid to flow in the inhalation direction through the two outlet cavities 304 and 306, as described above. In addition, as also described above, the medical device 200 may include an apparatus or structure which substantially (e.g., effectively) prevents fluid flowing in the exhalation direction from flowing through the inlet cavities 302, 308. Such apparatuses or structures may include one or more one-way valves, which will be now discussed in detail with respect to FIG. 5.

Referring now to FIG. 5, an embodiment of the medical device 200 including an exemplary one-way valve member 500 is shown. The one-way valve member 500 may include any suitable valve member known in the art. For example, the one-way valve member 500 may comprise of a pair of valve leaflets 502 and 504 arranged and configured to define an opening 506 therebetween for permitting fluid to flow through the valve in one direction, while restricting fluid flow in an another (e.g., substantially opposing) direction.

In one embodiment, an exemplary one-way valve member 500 may be placed within the second outlet cavity 304, for example. In such embodiments, therefore, during the respiratory cycle, the valve member 214 in the second position B (as shown in FIG. 4C) permits the fluid to flow through the first inlet cavity 302. The fluid passes through the lumen 212 of the second leg 208 to feed a first lung region. Once the fluid inflates the first lung region, a positive pressure may be built in the lung as compared to the atmospheric pressure, which allows the fluid to be exhaled. This positive pressure switches valve member 214 to the first position A (as shown in FIG. 4B) allowing the fluid to flow in the exhalation direction while coming out of the second outlet cavity 304. In particular, the positive pressure moves the one-way valve member 500 to switch to an open state, which opens the valve leaflets 502 and 504 to permit the fluid to flow through the opening 506. Those of ordinary skill in the art will readily recognize that one-way valve members 500 may be appropriately configured and disposed in one or all of cavities 302, 304, 306, 308, as desired. In embodiments where a suitable one-way valve member is disposed in a cavity (such as, e.g., cavities 304, 306) configured to transport exhaled fluid from the patient's lung out of the body, such valves may be disposed to allow fluid in a direction opposite to the direction of fluid flow allowed by valves 500 in cavities (e.g., cavities 302, 308) configured to transport inhaled air into the patient's lung. As such, when a personal exhales, the valves 500 in the cavities, such as, e.g., cavities 302, 308 configured to transport inhaled air into patient's lung may be configured to prevent exhaled air from flowing in the reverse direction through cavities 302, 308. As a result, exhaled air is directed through only those cavities (such as, e.g., cavities 304, 306) configured to transport exhaled fluid from the patient's lung out of the body, thereby causing valve member 214 to transition positions. In addition, exemplary embodiments of valve member 500 may be configured to restrict fluid flow until a predetermined pressure is achieved. Once pressure exceeds the predeterminate threshold pressure, a valve 500 may open, thereby allowing a fluid flow having an high velocity flow burst similar to, e.g., a cough, which may act against valve member 214 causing it to open.

In a further embodiment, one or more of cavities 302, 304, 306, and/or 304 may have differing configurations and/or dimensions. For example, one or both of "outlet" cavities 304, 306 may include a portion (such as, e.g., the opening disposed in a proximalmost surface of elongate tubular member 202) having a cross-sectional dimension smaller relative to a remainder of outlet cavities 304, 306. The smaller opening may cause the opening to function as a nozzle, thereby generating a higher flow velocity configured to impart relatively larger forces on valve member 214.

Turning now to FIG. 6, another embodiment of the medical device 200 is shown. In this embodiment, the medical device 200 may include a securing mechanism such as a first securing mechanism 602 and/or a second securing mechanism 604 coupled to the first leg 206 and/or the second leg 208, respectively. Both the first and the second securing mechanisms 602 and 604 may enhance coupling (e.g., anchoring) of the medical device 200 to the lung tissue. In particular, the first securing mechanism 602 may provide coupling of the first leg 206 to the surrounding tissue of, e.g., a first lung region, whereas the second securing mechanism 604 may provide coupling of the second leg 208 to the surrounding tissue of, e.g., a second lung region.

In the present embodiment, each of the first and the second securing mechanisms 602 and 604 may include one or more projections or barbs 606 projecting from the distal end 207 and 209 of the first and second legs 206 and 208, respectively. The barbs 606 may serve to anchor the legs 206 and 208 with the surrounding tissue of lung regions. Although three barbs 606 are depicted as projecting from each of distal ends 207 and 209, it should be contemplated that any suitable number of barbs may project from the distal ends 207 and 209 including, for example one, two, four, and so forth. In addition, structures other than barbs 606 also may be employed to enhance anchoring of medical device 200 to lung tissue. Suitable examples may include, but are not limited to, anchors, pins, sutures, expandable flexible mesh structures, and so forth.

Further, although each leg 206 and 208 may include a securing mechanism 602 and 604, it should be contemplated that either of the leg 206 and 208 may include one or more securing mechanisms. In addition, other portions of the medical device 200 such as elongate tubular member 202 may also include one or more securing mechanisms. For example, although not shown, the elongate tubular member 202 may include a flexible mesh structure disposed longitudinally along an external surface of the tubular member 202. The flexible mesh structure may be configured to expand when disposed within a body cavity, which may facilitate anchoring medical device 200 to the surrounding body cavity and/or tissue. Tubular member 202 may also include suitable projections or barbs 606.

The securing mechanisms 602 and 604 may be made from any suitable material known in the art. Exemplary materials include metals, polymers, alloys, or the like. According to an example, the securing mechanisms 602 and 604 may be made from a self-expanding material such as Nitinol.

Embodiments discussed above include the medical device 200 that may be implanted within the bronchial passageway 100 (as shown in FIG. 1A) to treat one or more pulmonary conditions such as COPD and/or emphysema. The medical device 200 may be implanted either temporarily or permanently within the bronchial passageway 100. An embodiment that will now be discussed with respect to FIG. 7 includes a medical device 200 that can be advanced within the bronchial passageway 100 temporarily during a medical procedure.

As shown in FIG. 7, the medical device 200 may be coupled to a sheath 702 having a central lumen 704 in fluid communication with the lumen 204 of the elongate tubular member 202. In particular, the sheath 702 may be operably coupled to the proximal portion 201 of the elongate tubular member 202 using suitable coupling structures and/or means known in the art, or by being integrally and continuously configured with the tubular member 202. Exemplary coupling structures may include snap-fitting, threading, gluing, welding, or the like. Those of ordinary skill will understand that sheath 702 may include a plurality of lumens (not shown) in communication with lumen 204. In some embodiments, one or more of the plurality of lumens may not be in communication with lumen 204.

In the present embodiment, the sheath 702 may include an intubation tube, which may be inserted inside the bronchial passageway of a patient for ventilation purposes. In such an instance, a proximal end (not shown) of the sheath 702 may remain external to the patient's body. In some embodiments, the valve member 214 may be operably coupled to a proximal end of the sheath 702 and may also remain outside of the patient's body. Although not shown, the proximal end of the sheath 702 may be coupled to a ventilation system. In some embodiments, the transition of valve member 214 between the first and second positions A and B, respectively, may employ one or more suitable actuating mechanisms. For instance, one or more balloons may be coupled to the medical device 200 and configured to switch valve member 214 between the two aforementioned positions (or any intermediate position) so as to close either the first or the second cavities 216 and 218 (as shown in FIGS. 4B and 4C). This may allow the ventilation system to permit the fluid (e.g., air) to selectively flow to either the first or second lung regions, as discussed previously, based on the instant positioning of the valve member 214.

Further, FIGS. 8A-8C illustrate another embodiment of the medical device 200 including another exemplary valve member 800.

As shown in FIG. 8A, the valve member 800 may include a rocker design having a pair of arms such as a first arm 802 and a second arm 804. The two arms 802 and 804 may be coupled together so as to define an angle α therebetween. In one embodiment, the arms 802 and 804 are coupled together so as to remain substantially perpendicular to one another. In addition, the valve member 800 may be coupled to a proximal most end of the medical device 200, similar to the valve member 214 discussed in previous embodiments. In addition, the valve member 800 may be configured to transition between first position and second positions so as to close or substantially close the first cavity 216 and the second cavity 218, respectively.

As discussed in previous embodiments, the valve member 214 includes a portion adapted to transition between the first and second positions (e.g., positions A and B) to close the two cavities 216 and 218, respectively. In such instances, the valve member 214 disposed in the first position (e.g., position A) has to travel an angle of almost 180 degrees to transition to the second position (e.g., position B) and vice-versa. In contrast, the valve member 800 includes two arms 802 and 804 aligned to each other at, e.g., approximately 90 degrees, which may enable the valve member 800 to rapidly transition between the two positions (e.g., positions A and B) because the arms 802 and 804 would need to only travel approximately 90 degrees. Discussed below are the embodiments having the valve member 800 present in the first position and the second position.

In particular, FIG. 8A shows the valve member 800 present in the first position (e.g., position A described in connection with the earlier embodiments). In such an embodiment, the fluid (e.g., air) may enter through the second inlet cavity 308 (as shown in FIG. 4B) and flows through the lumen 210 of the first leg, thereby feeding a first lung region. As shown, the first arm 802 of the valve member 800 may be in contact with a top surface 806 of the elongate tubular member 202. The second arm 804 may remain substantially perpendicular to the first arm 802 and thus to the top surface 806 of the tubular member 202. Of course, those of ordinary skill will understand that the second arm 804 may be disposed at any suitable angle relative to the first arm 802 and top surface 806.

Alternatively and additionally, FIG. 8B shows the valve member 800 present in the second position (e.g., position B described in connection with the earlier embodiments). In this case, the fluid enters through the first inlet cavity 302 (as shown in FIG. 4C) and flows through the lumen 212 of the second leg 208, thereby feeding a second lung region. In comparison with the embodiment shown in FIG. 8A, the second arm 804 of the valve member 800 may be in contact with the top surface 806 of the elongate tubular member 202, whereas the second arm 804 may remain substantially perpendicular to the first arm 802 and thus to the top surface 806 of the tubular member 202.

Further, the embodiments shown in FIGS. 8A-8B may include a first angle α and a second angle β. The first angle α includes the angle between the two arms 802 and 804 of the valve member 800, as described above. In one embodiment, the angle α may be approximately 90 degrees. Those skilled in the art, however, will appreciate that the first angle α may include any suitable angle such as an acute angle or an obtuse angle. Further, the second angle β may include an angle formed between a portion of the top surface 806 and the longitudinal sidewall of the elongate tubular member 202. In the illustrated embodiment, the second angle β may be approximately 90 degrees. Those skilled in the art, however, will appreciate that the second angle β may include any suitable angle.

FIG. 8C shows another embodiment having a slightly differing configuration. In this embodiment, the elongate tubular member 202 may include one or more curved sections such as curved sections 215 and 217 (as shown in FIG. 3A). As shown, the curved sections may be made around the periphery on the top surface 806 of the elongate tubular member 202 so as to form a third angle $β_1$ between the top surface 806 and the longitudinal sidewall of the elongate tubular member 202. In the illustrated embodiment, the third angle $β_1$ may substantially greater than the second angle β. For example, third angle $β_1$ may be approximately 135 degrees. However, those of ordinary skill in the art will understand that third angle $β_1$ may include any suitable angle.

Those skilled in the art will recognize that the present disclosure may be implemented in a variety of forms other than the specific embodiments described and contemplated herein. Accordingly, departure in forms and detail may be made without departing from the scope and spirit of the present disclosure as described in the appended claims.

What is claimed is:

1. A medical device for regulating fluid flow within one or more lungs of a patient, the medical device comprising:
    an elongate member having a proximal end, a distal end, and a plurality of channels extending therebetween;
    a first extension extending from the distal end of the elongate member and configured for placement in a first passageway of a lung, wherein the first extension defines at least one channel in communication with a first set of the plurality of channels;
    a second extension extending from the distal end of the elongate member and configured to be disposed in a second passageway of a lung, wherein the second passageway is different from the first passageway, and wherein the second extension defines at least one channel in communication with a second set of the plurality of channels; and a valve member operably coupled to a proximal end portion of the elongate member, wherein the valve member is configured to transition between a first position and a second position, wherein, in the first position, the valve member is configured to prevent fluid flow through the first set of the plurality of channels while the patient inhales, and, in the second position, the valve member is configured to prevent fluid flow through the second set of the plurality of channels while the patient inhales.

2. The medical device of claim 1, wherein the first and second extensions are configured to extend away from one another in a distal direction.

3. The medical device of claim 1, wherein the medical device is configured to transition between a compressed configuration and an expanded configuration.

4. The medical device of claim 1, wherein a portion of the medical device includes a wire scaffolding.

5. A medical device for regulating fluid flow within one or more lungs of a patient, the medical device comprising:
an elongate member having a proximal end, a distal end, a first channel, a second channel, a third channel, and a fourth channel each extending between the proximal end and the distal end;
a valve member operably coupled to a portion of the elongate member, wherein the valve member is configured to transition between a first position and a second position by fluid flowing through the elongate member, wherein, in the first position, the valve member is configured to prevent fluid flow through the first channel and the third channel while the patient inhales, and wherein, in the second position, the valve member is configured to prevent fluid flow through the second channel and the fourth channel while the patient inhales, wherein the valve member is configured to transition from the first position to the second position while the patient exhales and fluid flows proximally through the third channel, and wherein the valve member is configured to transition from the second position to the first position while the patient exhales and fluid flows proximally through the fourth channel.

6. The medical device of claim 5, further including a first extension extending from the distal end of the elongate member and configured for placement in a first passageway of the lung, wherein the first extension is disposed at an angle relative to a longitudinal axis of the elongate member, and wherein the first extension defines at least one channel in communication with the first channel and the second channel; and a second extension extending from the distal end of the elongate member and configured for placement in a second passageway of the lung, wherein the second passageway is different than the first passageway.

7. The medical device of claim 1, wherein, in the first position, the valve member is configured to cover proximal openings of the first set of the plurality of channels, and, in the second position, the valve member is configured to cover proximal openings of the second set of the plurality of channels.

8. The medical device of claim 1, wherein the valve member is configured to transition from the first position to the second position while the patient exhales and fluid flows proximally through a channel of the first set of the plurality of channels, and wherein the valve member is configured to transition from the second position to the first position while the patient exhales and fluid flows proximally through a channel of the second set of the plurality of channels.

9. The medical device of claim 1, further including a division extending through the elongate member, wherein the first set of the plurality of channels are disposed on a first side of the division, and the second set of the plurality of channels are disposed on a second side of the division that opposes the first side.

10. The medical device of claim 9, wherein the valve member extends along a proximal end of the division along an axis and is configured to pivot about the axis between the first position and the second position.

11. A medical device for regulating fluid flow within one or more lungs of a patient, the medical device comprising:
an elongate member having a proximal end, a distal end, a first channel, a second channel, a third channel, and a fourth channel each extending between the proximal end and the distal end;
a valve member operably coupled to a proximal end portion of the elongate member, wherein the valve member is configured to transition between a first position and a second position, wherein, in the first position, the valve member is configured to cover proximal openings of the first channel and the third channel, and, in the second position, the valve member is configured to cover proximal openings of the second channel and the fourth channel.

12. The medical device of claim 11, further including a division extending through the elongate member, wherein the first channel and the third channel are disposed on a first side of the division, and the second channel and the fourth channel are disposed on a second side of the division that opposes the first side.

13. The medical device of claim 12, wherein the valve member extends along a proximal end of the division along an axis and is configured to pivot about the axis between the first position and the second position.

14. The medical device of claim 12, wherein openings of the first channel and the third channel extend proximally and radially outward from the division in a first direction.

15. The medical device of claim 14, wherein openings of the second channel and the third channel extend proximally and radially outward from the division in a second direction that opposes the first direction.

16. The medical device of claim 11, wherein the valve member is configured to transition from the first position to the second position while the patient exhales and fluid flows proximally through the third channel, and wherein the valve member is configured to transition from the second position to the first position while the patient exhales and fluid flows proximally through the fourth channel.

17. The medical device of claim 11, further including a first extension extending from the distal end of the elongate member and configured for placement in a first passageway of a lung, wherein the first extension defines at least one channel in communication with the first channel and the second channel, and a second extension extending from the distal end of the elongate member and configured to be disposed in a second passageway of a lung, wherein the second passageway is different from the first passageway, and wherein the second extension defines at least one channel in communication with the third channel and the fourth channel.

* * * * *